US008002734B2

(12) United States Patent
Bassarab et al.

(10) Patent No.: US 8,002,734 B2
(45) Date of Patent: Aug. 23, 2011

(54) DUAL CHAMBER CONTAINER AND PROCESS FOR ITS FILLING UP

(75) Inventors: Stefan Bassarab, Biberach (DE); Alexander Bauer, Biberach (DE); Nicole Denkinger, Biberach (DE); Patrick Garidel, Norderstedt (DE); Markus Hemminger, Biberach (DE); Hans-Hoachim Kern, Mittelbiberach (DE); Andreas Langer, Maselheim (DE); Ingo Presser, Biberach (DE)

(73) Assignee: Boehringer Ingelheim International Gmbh, Ingelhheim am Rhein (DE)

( * ) Notice: Subject to any disclaimer, the term of this patent is extended or adjusted under 35 U.S.C. 154(b) by 0 days.

(21) Appl. No.: 11/464,493

(22) Filed: Aug. 14, 2006

(65) Prior Publication Data
US 2007/0129673 A1 Jun. 7, 2007

(30) Foreign Application Priority Data
Aug. 13, 2005 (DE) .......................... 10 2005 038 495

(51) Int. Cl.
*A61M 37/00* (2006.01)
(52) U.S. Cl. .............................. 604/82; 604/85; 604/89
(58) Field of Classification Search .................. 604/48, 604/82–85, 88–92, 181, 187, 191, 207
See application file for complete search history.

(56) References Cited

U.S. PATENT DOCUMENTS

| | | | |
|---|---|---|---|
| 1,961,023 A | 5/1934 | West | |
| 2,393,578 A | 1/1946 | Waite | |
| 3,025,991 A * | 3/1962 | Gillon | 215/311 |
| 3,326,215 A | 6/1967 | Sarnoff et al. | |
| 3,454,178 A | 7/1969 | Bender et al. | |
| 3,810,469 A | 5/1974 | Hurschman | |
| 4,036,225 A | 7/1977 | Maury | |
| 4,048,999 A * | 9/1977 | Kobel | 604/90 |
| 4,254,768 A | 3/1981 | Ty | |
| 4,479,578 A | 10/1984 | Brignola et al. | |
| 4,488,656 A | 12/1984 | Fukuoka et al. | |

(Continued)

FOREIGN PATENT DOCUMENTS
AU        2003236878 A1    10/2003
(Continued)

OTHER PUBLICATIONS
International Preliminary Report on Patentability and Written Opinion for corresponding application PCT/EP2006/065238.
(Continued)

*Primary Examiner* — Nicholas D Lucchesi
*Assistant Examiner* — Quynh-Nhu H Vu
(74) *Attorney, Agent, or Firm* — Michael P. Morris; David L. Kershner

(57) ABSTRACT

A double chamber container for holding and combining a solid lyophilizate and a liquid reconstituting medium, comprising a cylindrical body with a closure at each of the two ends, an upper displaceable closure at the reconstituting medium end, and a lower closure at the lyophilizate end, a separating stopper that can be pushed in the cylindrical body and act as a seal between the upper chamber and the lower chamber, and a bypass arranged underneath the separating stopper, with a length L that is preferably greater than the height H of the separating stopper, wherein at the upper end in the wall of the cylindrical body or in the separating stopper means are provided that allow partial connection of the interior of the cylindrical body to the environment during the lyophilization.

9 Claims, 7 Drawing Sheets

U.S. PATENT DOCUMENTS

| | | | |
|---|---|---|---|
| 4,929,230 A * | 5/1990 | Pfleger | 604/90 |
| 4,994,043 A * | 2/1991 | Ysebaert | 604/191 |
| 5,125,892 A | 6/1992 | Drudik | |
| 5,279,606 A | 1/1994 | Haber et al. | |
| 5,637,087 A | 6/1997 | O'Neil et al. | |
| 5,637,100 A | 6/1997 | Sudo | |
| 5,779,668 A | 7/1998 | Grabenkort | |
| 5,785,683 A | 7/1998 | Szapiro et al. | |
| 5,788,670 A | 8/1998 | Reinhard et al. | |
| 5,817,056 A * | 10/1998 | Tanaka et al. | 604/89 |
| 5,899,881 A | 5/1999 | Grimard et al. | |
| 6,419,656 B1 | 7/2002 | Vetter et al. | |
| 6,440,101 B1 | 8/2002 | Grabenkort et al. | |
| 6,602,223 B2 | 8/2003 | Szapiro et al. | |
| 2002/0068910 A1 | 6/2002 | Szapiro et al. | |
| 2002/0198498 A1 | 12/2002 | Porat et al. | |
| 2003/0199816 A1 | 10/2003 | Ramming | |
| 2007/0060875 A1 | 3/2007 | Bassarab et al. | |
| 2007/0060876 A1 | 3/2007 | Bassarab et al. | |
| 2007/0060877 A1 * | 3/2007 | Bassarab et al. | 604/89 |
| 2007/0129673 A1 | 6/2007 | Bassarab et al. | |
| 2009/0182301 A1 | 7/2009 | Bassarab et al. | |

FOREIGN PATENT DOCUMENTS

| | | |
|---|---|---|
| CH | 621524 | 2/1981 |
| DE | 1909794 | 2/1965 |
| DE | 1930803 | 1/1966 |
| DE | 1961166 | 6/1967 |
| DE | 1491781 | 10/1969 |
| DE | 1809892 | 6/1970 |
| DE | 1815118 | 6/1970 |
| DE | 2546495 | 4/1977 |
| DE | 3213072 | 11/1982 |
| DE | 3311525 | 10/1984 |
| DE | 3736343 | 5/1989 |
| DE | 4445969 | 3/1996 |
| EP | 0097880 | 1/1984 |
| EP | 0295337 | 12/1988 |
| EP | 0718002 | 6/1996 |
| EP | 1038543 | 9/2000 |
| EP | 1145703 | 10/2001 |
| EP | 1213036 | 6/2002 |
| FR | 1167766 | 11/1958 |
| FR | 2096680 | 2/1972 |
| FR | 2285150 | 5/1976 |
| GB | 730148 | 5/1955 |
| GB | 982744 | 2/1965 |
| WO | 93/04951 | 3/1993 |
| WO | 95/32015 | 11/1995 |
| WO | 98/01174 | 1/1998 |
| WO | 01/91836 | 12/2001 |
| WO | 03/084840 | 10/2003 |
| WO | 2007020237 A1 | 2/2007 |
| WO | 2007020238 A2 | 2/2007 |
| WO | 2007020240 A1 | 2/2007 |

OTHER PUBLICATIONS

International Search Report for International Application PCT/EP2006/065236.
International Search Report for International Application PCT/EP2006/065238.
International Search Report for International Application PCT/EP2006/065240.
International Search Report for International Application PCT/EP2006/065241.
"Die Lyophilisierung von Arzneimittenln in Fertigspritzen" by Von H. Vetter., Pharmazeutishe-Industrie-46th-year-10-pg-1045.
U.S. Appl. No. 11/464,491.
U.S. Appl. No. 11/464,492.
U.S. Appl. No. 11/464,494.
International Preliminary Report on Patentability and Written Opinion for PCT/EP2006/065236.
International Preliminary Report on Patentability and Written Opinion for PCT/EP2006/065240.
International Preliminary Report on Patentability and Written Opinion for PCT/EP2006/065241.
Von H. Vetter, "Lyophilization of pharmaceuticals in prefilled syringes", Pharm. Ind. 46, No. 10 p. 1045-1051 (1984).
International Preliminary Report on Patentability and Written Opinion for PCT/EP2006/065238.
Abstract in English (AU3186297) for WO98-001174, publication date Feb. 2, 1998.
Abstract in English (AU6643994) for WO-95-032015, publication date Dec. 18, 1995.
Abstract in English for DE1815118, publication date Jun. 25, 1970.
Abstract in English for DE3311525, publication date Oct. 4, 1984.
Abstract in English for DE3736343, publication date May 11, 1989.
Vetter, Von H. "Lyophilization of pharmaceuticals in prefilled syringes". Science+Technology, Pharm. Ind. 46, No. 10, 1984, p. 1045-1049, translated to English.
Office Action for related U.S. Appl. No. 11/464,494, May 31, 2011.

* cited by examiner

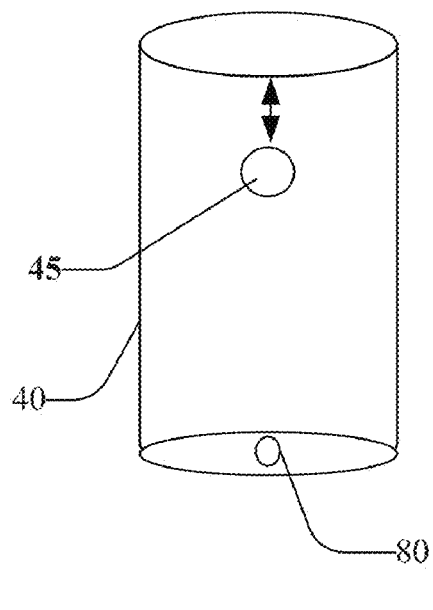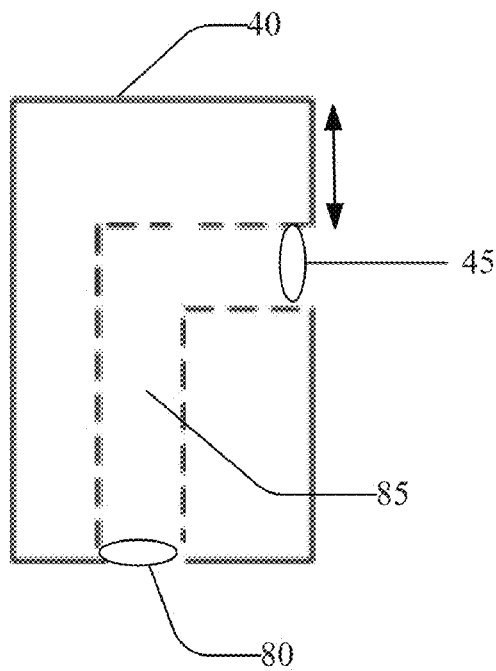
Fig. 7a  Fig. 7b
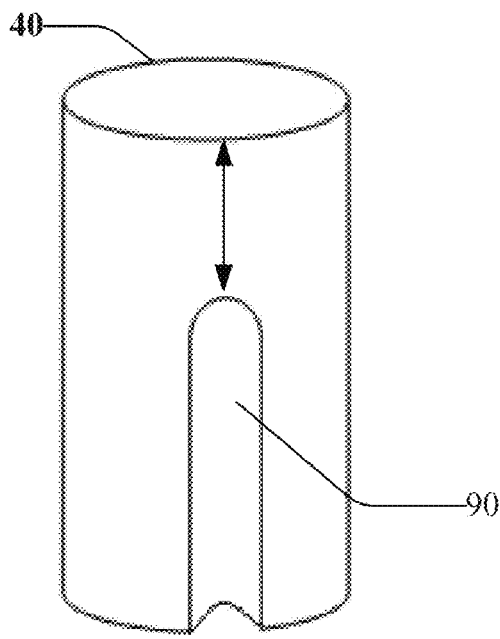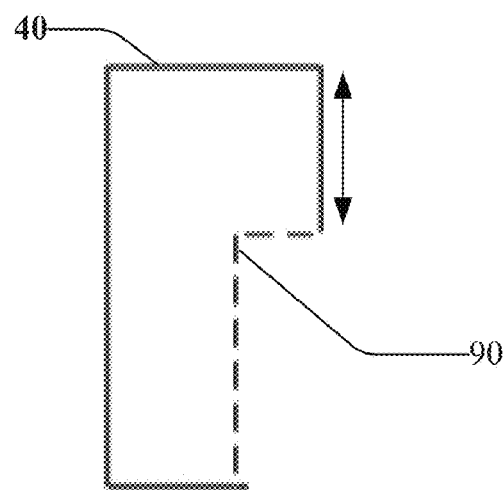
Fig. 7c  Fig. 7d

DUAL CHAMBER CONTAINER AND PROCESS FOR ITS FILLING UP

This application claims benefit under 119(a) of DE 10 2005 038 495, which was filed on Aug. 13, 2005, and which is incorporated herein by reference in its entirety.

BACKGROUND OF THE INVENTION

1. Field of the Invention

The present invention relates to a double chamber container which is particularly suitable for lyophilization, a method of filling the double chamber container, a method of mixing the two components contained therein and the use of the container.

2. Description of the Prior Art

There are pharmaceutical compositions which in their liquid state very rapidly lose their efficacy. To enable these compositions to be used in spite of their short shelf life, special devices and methods of lyophilization have been developed. Thus, pharmaceutical preparations which cannot be used in solution over long periods may be made durable by lyophilization, for example, and possibly stored away from light. The dry substance is only dissolved again, i.e., reconstituted, immediately before use. For this purpose two-component systems have become known for re-dissolving the lyophilizate immediately before use.

As is known, lyophilizates are also used in ready-prepared syringes with two chamber systems, the lyophilizate and solvent being stored separately and only combined just before use. Two-chamber prepared syringes of this kind have already been described in "Die Lyophilisierung von Arzneimitteln in Fertigspritzen", H. Vetter, Die Pharmazeutische Industrie, Jg. 46, 1984, Nr. 10, S. 1045-1049. Specifically, ready made syringes of this kind are constructed so that each of the components is housed in its own chamber, the chambers being arranged axially one behind the other and only brought into contact with one another immediately before use, so that the liquid component in one chamber can flow into the dry component in the other chamber.

In the prior art, other solutions have been sought for carrying out lyophilization of the solid substance present in the solution using double chamber systems of this kind, to produce a product which can be re-dissolved subsequently or after corresponding storage before use, i.e., to allow the two-component systems to be mixed together, while maintaining the sterility of the two components. The lyophilization of solutions in a syringe is only possible under special conditions, one problem being that during the lyophilization only a very small cross sectional area is available for the exchange of gases. The prior art contains numerous proposals for solving these problems.

The patents and patent applications described in the following paragraphs, namely DE 33 11 525, U.S. Pat. No. 5,788,670, EP 0 718 002 A2, U.S. Pat. No. 4,254,768, and EP 0 295 337 B1 are incorporated herein by reference in their entireties.

For example, a multi chamber disposable syringe is known according to DE 33 11 525, in which the lyophilizate is present in the syringe cylinder, particularly in the first syringe chamber adjacent to the neck of the syringe, which is separated from the second syringe chamber by the syringe plunger. The freeze drying, which is designed particularly for a vessel with a narrow opening, is carried out through two openings, e.g., using a hollow needle passed through the neck of the syringe into the first syringe chamber, this needle being connected to an ice condenser and a vacuum pump, while a second opening in provided through the free annular space between the hollow needle and the neck of the syringe, through which dry gas is passed. Two hollow needles may also be stuck through the elastic plunger body from the rear end of the syringe cylinder and in this way the liquid product in the first syringe chamber can be freeze dried.

According to the disclosure of U.S. Pat. No. 5,788,670, a double chamber syringe which can be broken down into two parts is described, wherein two medicinal components are introduced into the separate cylinders, the medicament in the lower part of the cylinder can be subjected to lyophilization, the two cylinder parts are then sealed and joined together.

Similarly, EP 0 718 002 A2 describes a two-chamber syringe having a syringe cylinder consisting of two part-cylinders. For lyophilization the syringe head can be provided with a closure cap with axially extending recesses which provide a connection to atmosphere in the only partially fitted state. The lyophilization is carried out with a part cylinder. The weak point of such a construction is the connection between the two chambers which, if the seal is inadequate, not only constitutes a possible site of contamination but also means that the liquid substance will run out during the mixing. An additional step is needed to join the two part-cylinders together, and this has to meet extremely stringent requirements. Furthermore, the closure cap has the disadvantage that precise adjustment has to be carried out to ensure that the recesses in the closure cap communicate with the outside, which is not readily possible, as the recesses are covered by the cap, on account of its shape, and therefore it is not easy to tell which position the recesses are in. Furthermore, it is not possible to connect to such a recess, and this may have advantages during lyophilization, for example. The closure also has to be adapted to the particular shape of a syringe head.

According to U.S. Pat. No. 4,254,768 a double chamber syringe also consists of two separate cylinders which can be fitted together. In the upper cylinder a ventilation slot may be provided in the side wall which is closed off when the two cylinders are pushed together and by the provision of an elastomeric ring. The assembly of the two syringe halves has to be carried very precisely, and there is the danger that if the two cylinders are not properly secured against moving relative to one another the venting slot will be exposed again and the system will be unsealed and exposed to contamination. Therefore, particular laborious measures have to be taken to prevent this.

Finally, EP 0 295 337 B1 discloses a double chamber syringe for a solid and liquid medicament, wherein the first lower chamber a towards the head of the syringe contains liquid substance, which is separated by a double ended bypass and a stopper from a second upper chamber b in which a solution can be lyophilized, the wall of the chamber b having a small opening so that the solvent can escape during the lyophilization. A disadvantage of this proposal is that there is a relatively small gap between the opening and the lyophilizate solution, so that when vacuum is applied there is a risk that some of the solution will be expelled from the cylinder. Therefore, the opening is also made correspondingly small, as a result of which much less gas can escape per unit of time. Another problem is that after the lyophilization and sealing the solid is at the top of the double chamber syringe and the liquid is at the bottom, so that the upper stopper is pressed onto the solid, where it will probably remain. After the stopper has been pushed into the double bypass the liquid contained in the lower chamber has to be allowed to move upwards towards the solid in the upper chamber, which is not readily possible. To achieve this, the syringe has to be rotated or shaken repeatedly, for example, in order to rinse the solid out of the upper chamber and force it into the lower chamber where the connection for the injection needle is located. It is impossible to prevent some solid residues remaining on the upper stopper, resulting in incomplete reconstitution.

The disadvantages described above show that there is still a need for an easy to operate device for reliably storing and mixing two-component systems, of which one component is a solid, particularly a lyophilizate, and the other is a dissolving/dispersing medium therefor. In particular it should be possible to carry out lyophilization directly in the device, while avoiding the disadvantages of the prior art. Contamination from outside should be ruled out as far as possible. In particular, subsequent mixing should take place without removing the components from the sterile inner part of the device and without any external intervention in the system thereby compromising the sterile condition. The device should also be easy to store. Furthermore, a method of easily filling a device of this kind should be provided. The device and the method should be usable on an industrial scale.

SUMMARY OF THE INVENTION

The objective described above is achieved by means of the features of claim 1. This provides a double chamber container for separately holding and combining a solid lyophilizate and a liquid reconstitution medium therefor, comprising
  a cylindrical body having a closure at each of the two ends of the body, an upper displaceable closure, particularly a stopper, at the reconstitution medium end and a lower closure at the lyophilizate end,
  a separating stopper, which can be moved by the application of pressure, in the cylindrical body as a seal between the upper chamber and lower chamber, the separating stopper having a side surface, a top and a bottom, and
  a bypass arranged underneath the separating stopper with a preferred length L greater than the height of the separating stopper, whereby
  at the upper end in the wall of the cylindrical body and/or in the separating stopper, means are provided which allow partial connection of the interior of the cylindrical body to the atmosphere during lyophilization.

The means may be selected from: (a) at least one opening through the wall of the cylindrical body of a defined size or at a defined spacing from the upper end of the cylindrical body, and/or (b) at least one through-opening extending inside or on the outside of the separating stopper, which extends from the side face of the separating stopper to and through its bottom, the opening in the side face of the separating stopper being of a defined size or arranged at a defined spacing from the bottom of the separating stopper.

BRIEF DESCRIPTION OF THE FIGURES

The accompanying Figures illustrate the device according to the invention and the procedural teaching which is to be carried out according to the invention without restricting the invention thereto. Specifically:

FIG. 7a shows a variant of a stopper with an opening in the side face and an interior channel according to an embodiment.

FIG. 7b is a side wise cross sectional view of the stopper shown in FIG. 7a.

FIG. 7c shows another variant of the stopper with an exterior channel on the outside of the stopper.

FIG. 7d is a side cross sectional view of the stopper shown in FIG. 7c.

In the Figures, similar parts bear the same reference numerals.

LIST OF REFERENCE NUMERALS

Figure 1:
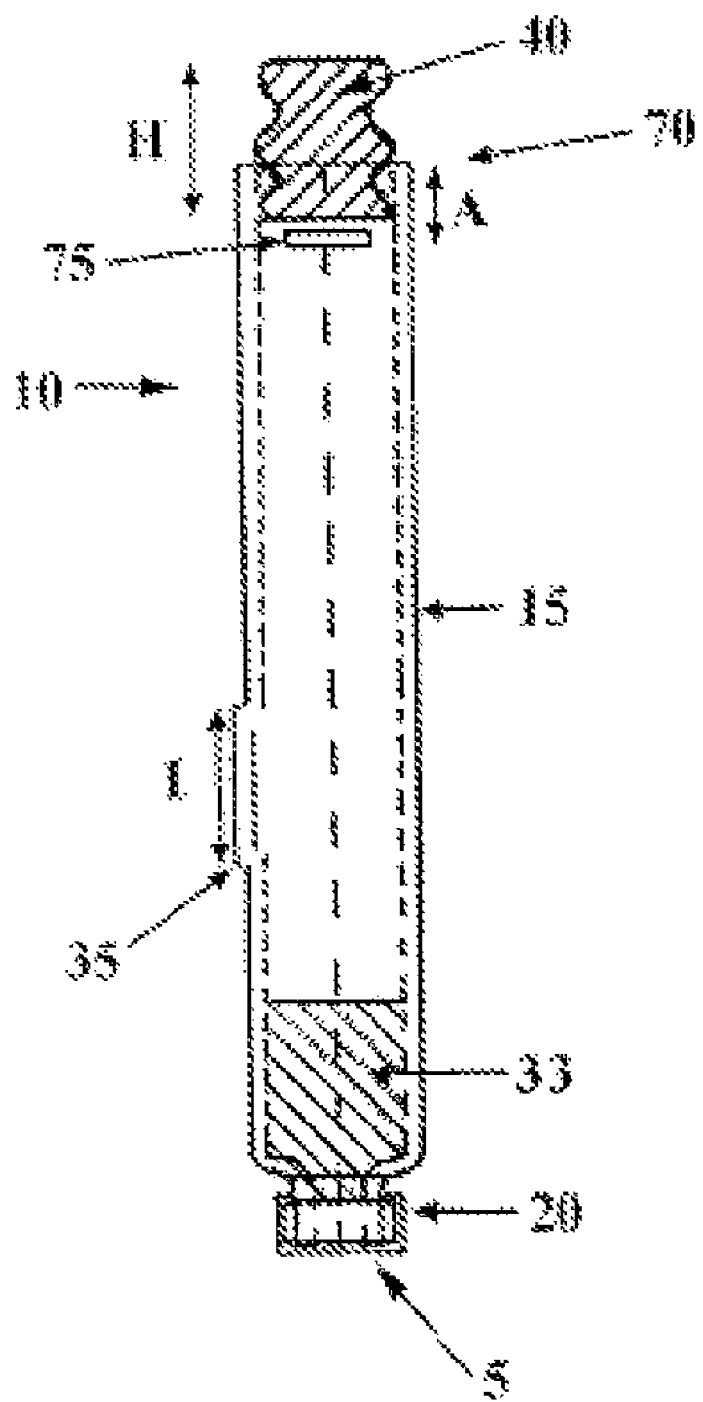
FIG. 1 is a schematic representation of a container according to the invention with a lateral opening according to variant (a) in the partly closed state (first position of the separating stopper)

5 lower end on the solid side
10 container
15 cylindrical body
20 closure, mouth
30 chamber containing solid component
33 lyophilization solution
35 bypass of length L
40 separating stopper of height H
45 lateral opening in the separating stopper
50 chamber containing liquid component
60 closure, stopper
70 upper end on the liquid side
75 lateral opening at the upper end

DETAILED DESCRIPTION OF THE INVENTION

The objective described above is achieved by means of the features of claim 1. This provides a double chamber container for separately holding and combining a solid lyophilizate and a liquid reconstitution medium therefor, comprising
  a cylindrical body having a closure at each of the two ends of the body, an upper displaceable closure, particularly a stopper, at the reconstitution medium end and a lower closure at the lyophilizate end,
  a separating stopper, which can be moved by the application of pressure, in the cylindrical body as a seal between the upper chamber and lower chamber, the separating stopper having a side surface, a top and a bottom, and
  a bypass arranged underneath the separating stopper with a preferred length L greater than the height of the separating stopper, whereby
  at the upper end in the wall of the cylindrical body and/or in the separating stopper, means are provided which allow partial connection of the interior of the cylindrical body to the atmosphere during lyophilization.

The present invention thus represents a one-piece container specially designed for lyophilization having a double chamber system. Special means are provided by which it is possible to at least partly connect the interior of the container to the outer environment. The means are arranged such that a stopper at the upper end of the container can assume two positions. In a first position of a stopper, during lyophilization gaseous solvent can escape outwards from the cylindrical container. This stopper is the separating stopper according to the invention. In a second position this stopper closes off the upper end of the cylindrical body in leak tight manner.

The means according to the invention may be selected from
(a) at least one opening through the wall of the cylindrical body, arranged at a specified distance from the upper end of the cylindrical body; and/or
(b) at least one opening provided right through the separating stopper, extending from the side face of the separating stopper to and through its bottom, the opening in the side face of the separating stopper being arranged in a defined magnitude and/or at a defined spacing from the bottom of the separating stopper.

By the provision of (a) at least one opening through the wall at the upper end of the container and/or (b) at least one opening in the separating stopper as a connection to the outer environment a lyophilizate solution can be introduced into the container and lyophilized therein, while the solvent escapes through the opening or openings during the lyophilization.

In the filled state the container also serves to store or preserve the lyophilizate and a reconstitution medium therefor in separate chambers. The two components can be mixed together immediately before use without the need to open the container.

The invention is not restricted with respect to the nature of the two components, provided that the solid component is a lyophilizate and the other liquid component is a reconstitution medium for the lyophilizate. For example, a solid medicament may be used as the lyophilizate. By lyophilization or freeze drying is meant in the present instance the known freezing of a liquid product, after which the frozen product is dried by sublimation followed by desorption. The reconstitution medium is a dissolving or dispersing medium for the lyophilizate. By combining the two components it is possible for example to prepare an injectable solution either in dissolved or dispersed form. The reconstitution medium is preferably water but may also be some other solvent or mixture of solvents.

The cylindrical body according to the invention is an essentially elongate hollow body with two open ends which has preferably been formed integrally, i.e., made in one piece. The "cylindrical" body need not necessarily be cylindrical in shape, although this is the most common shape. Any other geometric shape for an elongate hollow body is possible, such as angular or oval, for example, in which case the closures and separating stopper and the like must be matched to the chosen shape. The material of which the cylindrical body consists or which it contains is not particularly restricted according to the invention. The container may be selected for example from plastics or glass. Glass is preferred on account of its transparency and its compatibility with numerous medical formulations. The cylindrical body therefore preferably consists of glass or contains glass, as this produces the least effect on the components contained therein and the body is preferably transparent. For particular requirements, however, other materials may be suitable, such as special plastics or the like. Medical safety is particularly important, as it is desirable that there be as little interaction as possible with the medium contained therein.

The double chamber container further comprises 2 closures, one of which is provided at the solid end (bottom end) while the other is provided at the liquid (upper) end of the container. The closure devices are not restricted further provided that the closure device at the liquid end enables pressure to be applied to the liquid for mixing the two components, so that the separating stopper moves out of its position and can be pushed into the bypass.

The upper closure is preferably a stopper which provides a suitable seal, is inert relative to the medium to be added, and satisfies the sterility conditions. The upper closure, particularly a stopper, should be of such a size or shape that any openings provided are sealed off by it in the second position of the stopper.

The lower closure is preferably a pierceable membrane having a flanged cap. It is also possible to provide a removable closure such as a sealing disc. If the container is a carpule, a rubber closure may be provided which can be pierced by an injection needle. However, any other closure known to the skilled man may also be used.

The separating stopper arranged in the cylindrical body defines the size/volume/dimensions of the two chambers and functions as a liquid barrier device for the liquid component, which is prevented from passing into the other chamber. The shape of the separating stopper is not particularly restricted. It has a suitable three-dimensional shape to ensure that the two chambers are sealed off from one another. The separating stopper may be of any suitable shape: cylindrical shapes, cylindrical shapes with rounded sides, dumbbell-shaped, cuboid, conical, truncated cone, or conical shapes.

In any case, when a force, particularly a manual force is exerted, the closure, particularly the stopper, should be movable at the upper end of the chamber and hence towards the liquid component.

The separating stopper is preferably an elastic and flexible material and is preferably made of rubber, caoutchouc, such as natural or synthetic rubber, plastics, such as elastomers, thermoplastics, thermoplastic elastomers and the like. The material of the separating stopper should provide a guaranteed seal between the two chambers, e.g., during storage.

According to a preferred embodiment according to the invention the separating stopper is of a suitable shape, size and/or material that on the one hand will prevent it from being pushed out of its initially fixed and defined position in the cylindrical body but on the other hand will assist the intended displacement of the separating stopper into the bypass. Conveniently, a balanced solution may be prepared by the suitable provision of a suitable shape with (adhesive) bumps, lips, beads or the like and/or by the choice of a suitable diameter.

In the present invention the term "form" is intended to refer to the outer shape or geometry. The term "size" is intended to refer to the dimensions, i.e., the ratios of magnitude.

The separating stopper preferably has a larger outer diameter than the internal diameter of the cylindrical body, so that sufficient pressure is built up between the inner wall and shaped member to close the interface, although the latter is movable in the container under the effect of force. The separating stopper is therefore mounted to be movable or displaceable and fluid tight within the container.

In order that lyophilization can be carried out with the container, means are provided which enable the solvent to escape from the container. According to variant (a) at least one opening is provided in the wall at the upper end of the cylindrical body with a defined size and/or at a defined spacing. A defined spacing from the upper end or a defined size means that these parameters are selected so that the opening or openings in the first position which the stopper can assume are not closed, i.e., there is a connection to the outer environment, but in a second position of the stopper the opening or openings can be closed. The opening or openings at the upper end of the container are therefore positioned or dimensioned such that they remain open as a result of the application or fitting of a stopper (first position), so that during the lyophilization a solvent is able to escape from the lyophilizate without any problem, but the open end of the container is closed off so that no foreign substances can get in. In the first position, therefore, the stopper covers only the upper end of the cylindrical container in this embodiment, but leaves the openings open. In the second position the stopper closes off both the lower end and also the opening or openings completely to provide a seal against the outer environment, e.g., at the end of the lyophilization.

According to the other variant (b) the separating stopper has at least one opening which provides a connection between the interior of the container and the outer environment, the separating stopper being fitted (in a first position) during the lyophilization in such a way that the upper end of the container is closed off but the opening or openings in the separating stopper remain open and a solvent can evaporate out of the lyophilizate without any problem. For example, one, two, three, four or more openings may be provided at the upper end of the cylindrical body with a defined size and/or at a defined spacing from the upper end of the cylindrical body (variant (a)) or with a defined size and/or at a defined spacing from the lower end or bottom of the separating stopper in the side face thereof, while the opening, either beginning at the side face of the separating stopper, extends into the interior of the separating stopper and passes right through it to the bottom of the separating stopper or at least part of the side face of the separating stopper has been recessed at a defined spacing from the lower end or bottom of the separating stopper or with a defined size (variant (b)). The defined spacing or the defined size is selected in both variants such that the separating stopper is able to close off the upper end of the cylindrical body without closing off the opening or openings at the upper end of the cylinder (variant (a)) and/or the opening or openings (or recess or recesses) in the side face of the separating stopper (variant (b)) (first position of the separating stopper). According to the invention, openings may simultaneously be provided at the upper end of the container and in or on the separating stopper.

During the lyophilization the separating stopper therefore has an essential function. During the lyophilization of the solution contained in the cylindrical body the solvent to be evaporated can therefore escape laterally from the packing means through at least one opening at the upper end of the container and/or the separating stopper.

According to the invention, preferably at least one opening may be provided on opposite sides of the upper end of the container and/or the separating stopper. The openings may also be provided in pairs and/or may be provided symmetrically, for example, over part or all of the region of the upper end and/or the separating stopper.

The opening or openings may be selected from round, oval, oblong, triangular, or rectangular openings, particularly slots or holes and may be arranged below one another and/or side by side. This is also intended to refer to recesses in the side or outer surface of the separating stopper, which then form an "opening" with the wall of the vessel. Opening or openings of this kind ensure that the cross sectional area is large enough for the exchange of gases during lyophilization.

In the cylindrical body there is also a bypass in the form of a detour line along the cylindrical body, which is located underneath the separating stopper, i.e., in the chamber containing the lyophilizate. The bypass is not particularly restricted provided that its length is greater than the height of the separating stopper, so that when the stopper is pushed into the bypass it opens up a passage for the reconstitution medium to enter the chamber containing the lyophilizate. In other words the bypass is a region in the cylindrical body which defines a bypass zone which is preferably longer along the longitudinal axis than the length of the separating stopper along the longitudinal axis, the bypass being arranged and having a size such that, as soon as the separating stopper has been pushed into the bypass zone and is located therein, the liquid component is able to flow around the stopper. The bypass provided underneath the separating stopper therefore preferably has a length L along its longitudinal axis which is greater than the height H of the separating stopper along its longitudinal axis. The bypass is therefore preferably longer than the stopper, thus producing a flow of liquid outside or through the stopper when the stopper is in the bypass position. When the separating stopper is in the bypass zone both ends of the bypass preferably project over it over the entire length.

The bypass may be provided with or without any alteration to the internal diameter, such as a widening of the internal diameter of the cylinder, i.e., a protuberance or cross sectional widening which extends radially outwards, for example, and alters the internal diameter of the container. In the other case the inner wall has a depression in the longitudinal direction, such as a channel or groove, without changing the internal diameter.

The bypass may be provided on one or more sides, i.e., on one or more sides of the container. Preferably it is provided on only one side of the inner wall of the container.

In the filled state for storage the separating stopper is located above the bypass zone and for mixing it is pushed into the bypass zone. Preferably, therefore, (adhesive) bumps, beads, or lips are provided in the bypass zone for securing the separating stopper there and ensuring unimpeded passage of the reconstitution medium to the solid component.

If the liquid is put under pressure, the separating stopper initially continues to adhere to the inner wall of the cylindrical body by frictional forces. If the frictional adhesion of the separating stopper to the wall of the cylindrical body is not sufficient for a particular application, to prevent accidental movement, the latter may additionally be provided with projections such as small beads, lips, or bumps for adhering to the inner wall of the cylindrical body. The pressure therefore does not increase in the other chamber. As a result, a differential pressure is produced between the two chambers. By the application of pressure the separating stopper is finally pushed in the direction of the bypass, as a result of which, as soon as the separating stopper is totally located in the bypass, the liquid component is able to flow into the other chamber and the two components are mixed together.

The invention also relates to a method of filling the double chamber container according to the invention, comprising the following steps:
(1) sealing a cylindrical body at the lower end;
(2) filling the cylindrical body with a lyophilization solution through the open upper end of the cylindrical body;
(3) putting a separating stopper on the open upper end in a first position, to allow gaseous solvent to escape outwards from the cylindrical body by suitable means;
(4) lyophilizing the lyophilization solution in the lyophilizer while allowing the gaseous solvent to escape through the means from the cylindrical body and obtaining a lyophilizate cake;
(5) pressing and inserting the separating stopper into the cylindrical body above the lyophilizate cake and above the bypass;
(6) filling the cylindrical body with reconstitution medium above the separating stopper and (7) sealing the upper end of the cylindrical body and the means optionally provided for the escape of solvent with a closure.

The process will hereinafter be described in detail; any individual features described in relation to the process also apply accordingly to the double chamber container and vice versa.

In a first step of the filling process according to the invention the lower end or the mouth of the cylindrical body is sealed. The lower end may for example be tapered outwards. The closure may be for example a stopper, a membrane, a disc, particularly a sealing disc, optionally with a cover, such as a covering cap or flanged cap, or the like. The closure is not particularly restricted as long as it provides a suitable seal, is inert with respect to the medium which is to be added, and meets the conditions of sterility. The lower closure is most particularly preferably a pierceable membrane with a flanged cap. It is also possible to provide a removable closure. If the container is a carpule or ampoule, a rubber closure may be provided which can be pierced with an injection needle. However, any other seal known in the art may also be used.

Then in step (2) the cylindrical body is filled with a lyophilization solution through the open upper end of the cylindrical body. This may be any desired solution which is to be lyophilized. One example might be a pharmaceutical composition which is made more durable by being lyophilized.

Then in step (3) a separating stopper is placed on the open upwardly directed end in a first position, while gaseous solvent is able to escape outwards from the cylindrical body through suitable means. These suitable means are those described according to variant (a) or b according to the invention or a combination of the two.

According to variant (a) at least one opening is provided at the upper end of the cylindrical body at a defined spacing and/or with a defined size. This spacing/size is selected so that a stopper can be fitted for the lyophilization onto the upper end of the cylindrical container in such a way that the opening or openings provided are not covered by the stopper but remain at least partly open to the outside. This stopper constitutes the eventual separating stopper which divides the cylindrical body into two chambers, i.e., the separating stopper which separates the lyophilizate from the reconstitution medium. What is essential to the variant (a) according to the present invention is that this separating stopper is only partially placed in the lower end of the glass body, so that the solvent can evaporate sideways during the lyophilization through the opening or openings in the cylindrical body. A lateral opening is sufficient but several lateral openings are preferred.

According to variant (b) the minimum of one opening is provided directly in the stopper. The opening or openings are arranged in the separating stopper according to this variant at defined spacing from the bottom of the separating stopper or with a defined size such that the stopper does indeed close off the open end of the container but the one, two, three or more openings in the separating stopper remain at least partly open, providing a communication between the interior of the cylindrical body and the outer environment. The opening or openings run laterally from the outer side face of the separating stopper into the interior of the stopper or on the outside of the separating stopper down to the underside or bottom of the separating stopper. What is essential to variant (b) of the present invention is that this separating stopper is only partly placed in the lower end of the cylindrical body, so that the solvent can escape through the opening in the stopper during lyophilization. A laterally mounted opening in the outer or side face of the stopper is sufficient, several lateral openings are preferred.

The openings are not particularly restricted as to their shape and size. They may be selected at will depending on the solvent which is to be eliminated and the volume to be removed. Possible embodiments of the openings at the lower end of the cylindrical body according to variant (a) of the invention are one or more round, oval, oblong, triangular or rectangular openings which may be arranged below one another and/or side by side, especially slots or holes. The openings may also be arranged at defined spacings from one another, like certain perforations, for example.

Possible embodiments of the openings in the separating stopper according to variant (b) of the invention are one or more openings such as channels which extend from one or more sides of the separating stopper to the bottom, such as round, oval, oblong, triangular or rectangular openings in the form of slots, holes or perforations, which are provided on the sides of the separating stopper, which open, for example, into an interior channel of the separating stopper which constitutes one or more openings in the bottom of the separating stopper or extend over the outside of the lateral or outer surface of the stopper.

The stopper and separating stopper are preferably rotationally symmetrical with respect to the central axis.

According to step (4) of the process the lyophilization is carried out in a manner known to the skilled man, with the solvent escaping through one or more openings at the upper end/separating stopper. The lyophilizer is of a standard commercial type, the process parameters of which are automatically regulated, for example.

After the lyophilization, in step (5) the cylindrical body is sealed in the lyophilizer by pressing in the stopper which was initially used as a closure for the upper end and is now the separating stopper in the cylindrical body. This pressing in may, for example, be partly carried out by the fact that the plates on which the cylindrical bodies stand are pushed together. The closing of the cylindrical body by the pressing in and fitting of the separating stopper above the lyophilizate cake is most preferably carried out under vacuum, so that it is possible to position the separating stopper at the desired place in the container without any difficulty. This may be carried out together with the pressing in or subsequently, e.g., using a filling machine. For this, a special mechanism may be set up for pressing in and fitting the stopper. Using this, the separating stopper can be pushed far enough into the cylindrical body without causing excess pressure in the chamber which has already been sealed. The cylindrical body which now contains the lyophilizate in the lower chamber which has already been sealed in the lyophilizer is then removed from the lyophilizer.

The opening or openings (or recess or recesses) which are optionally provided in or on the separating stopper are automatically closed by pressing in and positioning in the container by the inner wall thereof, so that it is not possible for one of the components to pass accidentally through the separating stopper.

Then the sealed container is taken to a filling station, where in step (6) it is filled with reconstituting medium through the top end of the cylindrical body which is now open again, i.e., the dissolving or dispersing medium is poured into the chamber above the separating stopper. After the container has been filled with reconstituting medium, i.e., a dissolving or dispersing medium for the lyophilizate, the container is fitted with a closure (step (7)). Preferably a stopper may be used as the upper closure. However, it is also possible to use any other closure known in the art, provided that it is displaceable under the effect of pressure. It is particularly advantageous if the upper closure at the liquid end is a stopper which contains an elastic material or consists thereof, such as plastics, rubber or rubber-like elastic material, such as elastomers, thermoplastics, elastomeric thermoplastics, etc.

The upper closure is designed so that it also closes off any opening(s) provided at the upper end, so as to seal the container completely.

It is particularly expedient if the stoppers and/or closure members are supplied and inserted by means of a washing and sterilizing device or an autoclave along sterile corridors. After the container has been sealed it is taken out of the sterile area through an airlock; finally it is labeled and packaged. It will be understood that in this process all the surfaces and equipment are designed for aseptic operation.

According to the invention the separating stopper thus performs a number of different functions: first of all during lyophilization it acts as a transitional closure which reduces contamination of the container from outside. The solvent is eliminated during the lyophilization through the minimum of one opening provided according to variant (a) and/or (b), which the separating stopper leaves at least partly open. Then the separating stopper is pressed into the container and thus acts as a temporary closure inside the cylindrical body, to protect the lyophilizate obtained from external influences. At the same time the position of the separating stopper defines the size of the two chambers in the container and acts as a separation and seal for the components contained in the two chambers, thus allowing separate storage without any problems even over length periods. Finally, in order to mix the two components, pushing the separating stopper into the bypass enables the liquid component to pass through to the solid component, producing the desired mixture. Because the separating stopper performs a number of functions, the embodiment according to the invention results in significantly easier filling and handling.

Preferably the double chamber container is a vessel for the separate storage of 2 substances, such as a carpule, which is intended for single or multiple uses.

The measurements of the double chamber container depend on the volume of the solution which is to be produced; in human medicine, volumes of 10 ml are rarely exceeded, which means that volumes of up to about 20 ml are sufficient. In exceptional cases and for veterinary use however it is possible to exceed these volumes by a long way.

The invention also relates to a method of mixing a solid lyophilizate and a liquid reconstitution medium in a double chamber container according to the invention, comprising
 a cylindrical body with a closure at each of the two ends of the body, a movable upper closure, particularly a stopper, at the reconstitution medium end, and a lower closure at the lyophilizate end,
 a separating stopper which can be moved by the application of pressure, in the cylindrical body, as a seal between the upper and lower chambers, the separating stopper having a side face, a top and a bottom, and
 a bypass arranged underneath the separating stopper, with a length L that is preferably greater than the height H of the separating stopper, wherein
 at the upper end in the wall of the cylindrical body and/or in the separating stopper means are provided which allow partial connection of the interior of the cylindrical body to the environment during the lyophilization,
comprising the steps of:
 applying pressure to the movable upper closure until the separating stopper is pushed into the bypass and
 allowing the liquid component to flow from the upper chamber into the lower chamber to obtain a mixture.

In order to mix the two components, the upper closure is pushed towards the separating stopper by the application of external force, particularly force exerted manually, and at the same time pressure is applied to the liquid end, causing the separating stopper to be pushed into the bypass, so that the liquid component has a passage to the chamber containing the solid component. The two components may thus be mixed together without affecting the sterile conditions of the double chamber container.

Preferably the upper closure is a stopper, particularly a rubber stopper. The two components are particularly preferably mixed together by holding the container vertically, i.e., with the lower closure, i.e., the solid end or mouth at the bottom. Preferably the closure has on the solid side a sealing disc with a flanged cap, but it is also possible to use any other suitable, optionally removable, closure.

The pressure on the upper closure or stopper may be applied using the fingers or a suitable punch. Both the reconstitution medium and the separating stopper then move downwards. The separating stopper moves into the bypass position and thus no longer forms a seal. The pressure exerted on the liquid component by the stopper allows the liquid to flow through the passage opened up by the bypass between the upper and lower chamber around the separating stopper and to enter the chamber containing the lyophilizate.

The reconstitution medium combines with the lyophilizate and the latter goes into solution. The closure or stopper at the other end can be pressed right through to the separating stopper. The solution is finally completely reconstituted and is ready for use.

The invention also relates to the use of the container according to the invention in human and veterinary medicine.

The present invention has a number of advantages:

According to the invention a double chamber container with a lyophilizate and a reconstitution solution is provided. Using the container according to the invention it is possible to dry a substance which is unstable in solution directly in the lyophilizer and then provide a double chamber system in the single chamber container. Thus the construction according to the invention allows problem-free storage of the two-component system without premature mixing and hence a loss of efficacy of the components taking place. The two-component system provided according to the invention may be stored in the sterilized, pre-filled state ready for use. The mixing of the two components takes place after storage immediately before use. The double chamber container can be thrown away after use.

Using the double chamber container according to the invention the desired solution may be prepared immediately before use, resulting not only in a fast and reliable system, but also ease of manufacture and filling. This is an all-in-one solution, i.e., a vessel is obtained having two chambers which are separated from one another by a stopper.

Using the double chamber container according to the invention it is possible to carry out reconstitution of a lyophilizate in a sealed two-chamber system, by simple maneuvers, without having to break the seal of the system in order to carry out the mixing, thereby opening it up to undesirable external microbial, chemical or physical influences.

The double chamber system described allows the container already in the lyophilizer to be tightly sealed. This gives rise to the advantages that contamination of the lyophilizate, particularly by particles, pathogens, and any foreign bodies, are avoided. Moreover, the lyophilizate is protected from moisture and oxygen. The container can be used as primary packaging and stored in its clearly labeled form. The use of two-component systems, particularly lyophilized preparations, can thus be made simpler. The container is not limited in any way and may be used for example in so called pen systems which are already on the market.

The inventive achievement further consists in providing a special container which is designed so that it is possible, either by means of special openings at one end of the container and/or by the provision of a special closure, particularly a stopper containing openings, to lyophilize through the end of the container and to seal the container actually in the lyophilizer.

The above description discusses a number of variations and suggests a range of possible modifications which will be immediately apparent to the skilled man.

Figure 2:
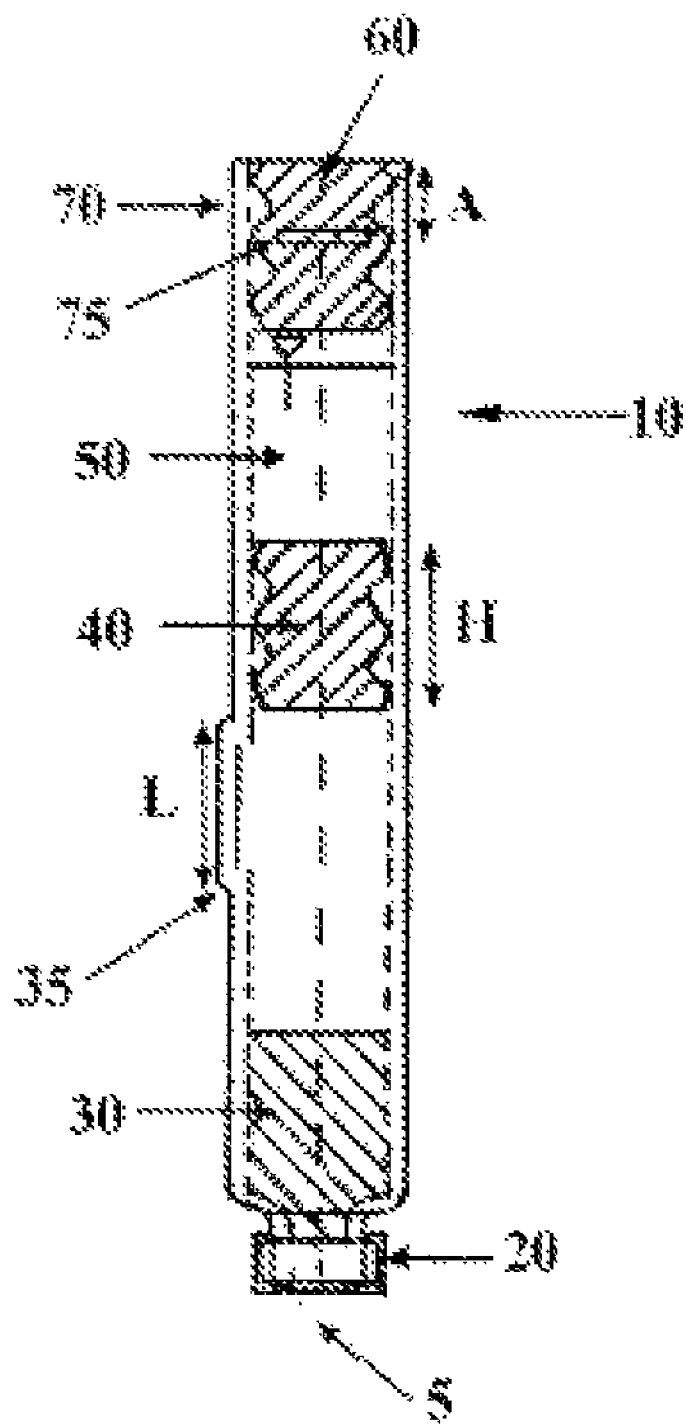
FIG. 2 is a schematic representation of a container according to the invention according to variant (a) in the filled, sealed state.

FIGS. 1 and 2 diagrammatically show a container 10 according to the invention according to variant (a) with a lateral opening 75 in the partly closed state (first position of the separating stopper 40) immediately before and during a lyophilization process (FIG. 1) and in the totally filled and sealed state (FIG. 2), i.e., filled with lyophilizate and reconstituting medium. Specifically, a cylindrical body 15 is shown which may be made of glass, for example. This is provided at one end 5 with a closure 20. This may be, for example, a sealing disc with a flanged cover. A lyophilization solution 33 has already been introduced into the cylindrical body 15 through the open upper end 70 of the cylindrical body 15. This may be any desired solution which is to be lyophilized. For example, it may be a pharmaceutical composition which is more durable when freeze-dried.

In the cylindrical body 15 there is also provided a bypass 35 the length L of which is preferably greater than the height H of the separating stopper 40. At the upper end 70 a separating stopper 40 is inserted in the open end 70 in such a way that a lateral opening 75 at the upper end 70 of the container 10 remains outwardly open (first position of the stopper 40). The opening 75 is shown as a slot in FIG. 1. Obviously, any desired opening of any desired shape may be provided which allows the solvent to leave the container during the lyophilization. The opening 75 is at a defined spacing A (shown by the double arrow in FIG. 1) from the upper end of the cylindrical body 15, so that the stopper 40 closes off the upper end 70 but not the opening 75 (first position).

Then freeze drying is carried out in the usual way in the lyophilizer, with the solvent evaporating from the lyophilization solution 33 through the opening 75. After the lyophilization, sealing is carried out in the lyophilizer by pressing the separating stopper 40 in at the upper end 70. In other words while still in the lyophilizer the separating stopper 40 is pushed down into a position in which it is arranged above the lyophilizate cake 30 obtained and above the bypass 35. This may be done partly, for example, by pushing together the plates on which the containers stand in the lyophilizer. The sealing of the container 10 may be carried out under vacuum, so that it is possible to subsequently push the separating stopper 40 further into the cylindrical body, optionally in a filling machine, without producing any excess pressure in the already sealed chamber. The containers 10 are then removed from the lyophilizer. The reconstituting medium is then added through the now exposed opening at the open end 70. Finally, the container 10 is sealed off with a closure 60 such as an end stopper which now also closes off the opening 75 (second position).

Figure 3:
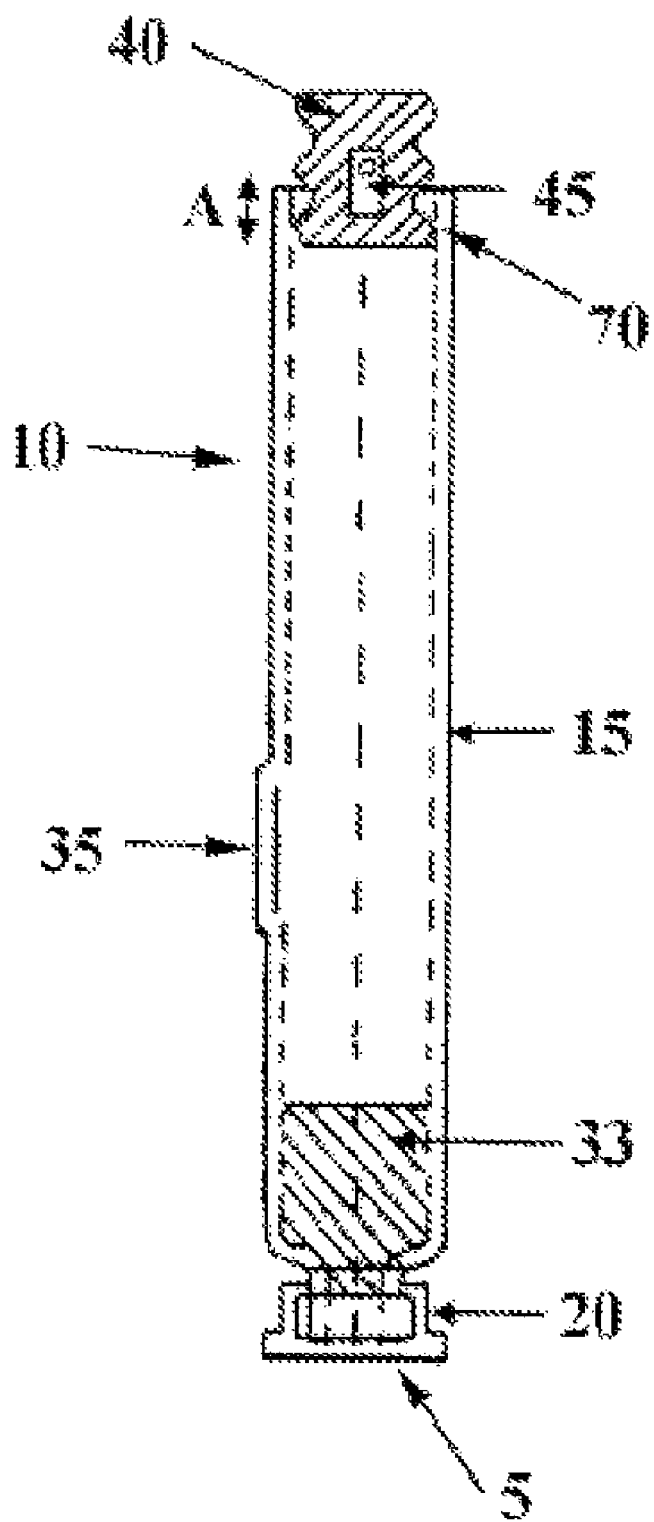
FIG. 3 is a schematic representation of a container according to the invention with a separating stopper with a lateral opening according to variant (b) in the partly closed state (first position of the separating stopper)
Figure 4:
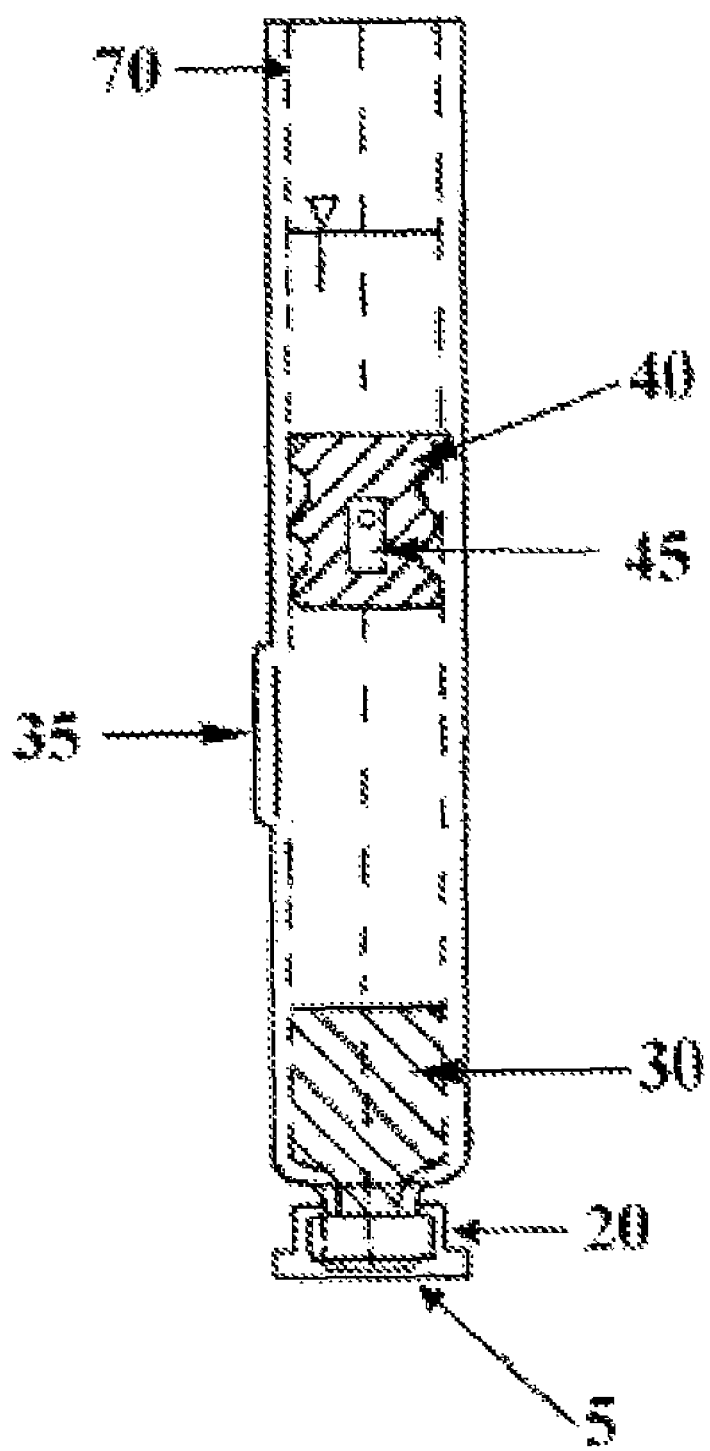
FIG. 4 shows a schematic representation of a container according to the invention with a separating stopper with a lateral opening according to variant (b), with the separating stopper positioned above the lyophilizate cake and above the bypass.
Figure 5:
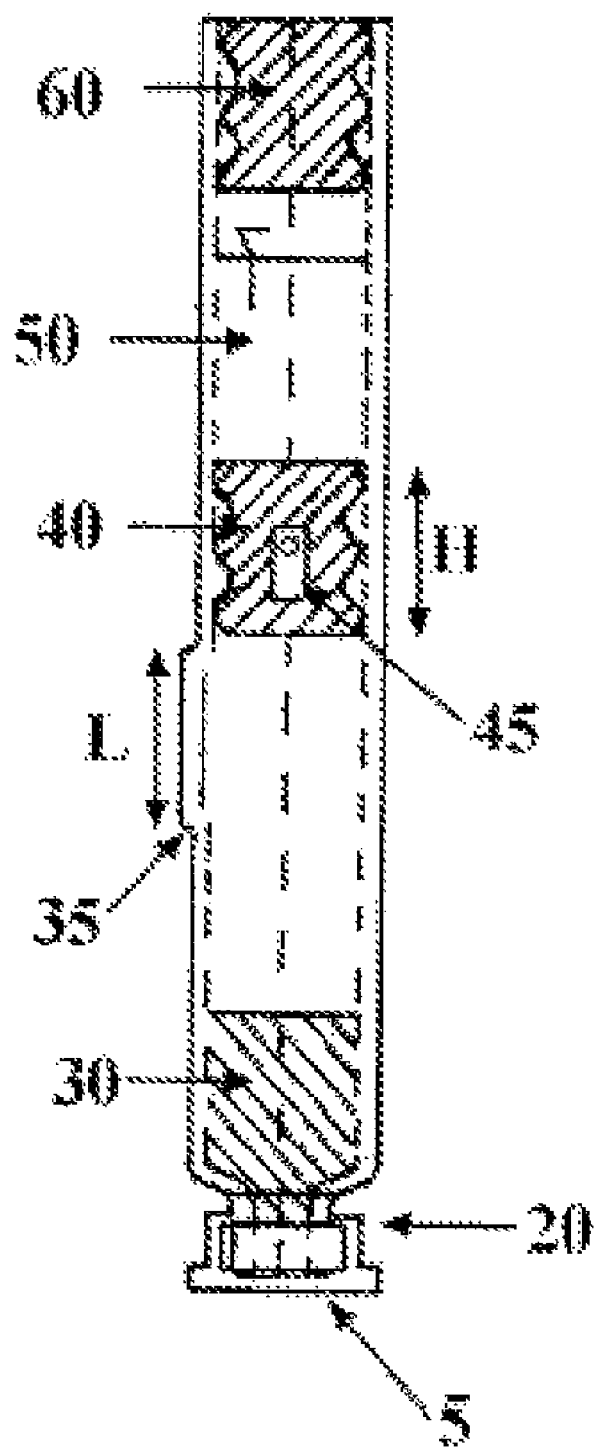
FIG. 5 shows a schematic representation of a container according to the invention with a separating stopper with a lateral opening according to variant (b) in the filled, sealed state (second position of the separating stopper)

FIGS. 3 to 5 show a schematic representation of a container 10 according to the invention, according to variant (b), with a lateral opening 45 in the separating stopper 40, in the partly closed state immediately before or during the lyophilization (FIG. 3) with lyophilizate and with the separating stopper 40 inserted immediately after the lyophilization (FIG. 4) and in the totally filled and sealed state (FIG. 5), i.e., filled with lyophilizate and reconstituting medium. Specifically, a cylindrical body 15 is shown which may be made of glass, for example. This is provided at one end 5 with a closure 20. This may be, for example, a sealing disc with a flanged cover. However, any closure, for example a removable one, is possible. A lyophilization solution 33 has been added to the cylindrical body 15 through the open upper end 70 of the cylindrical body 15. This may be any desired solution which is to be lyophilized. For example, it may be a pharmaceutical composition which is more durable as a result of lyophilization.

Also provided in the cylindrical body 15 is a bypass 35 the length L of which is preferably greater than the height H of the separating stopper 40. At the upper end 70 a separating stopper 40 is inserted in the open end in such a way that a lateral opening 45 in the separating stopper 40 forms a connection from the inside of the container 10 to the outer environment. The opening 45 is shown in FIG. 1 as a rectangular opening 45. Naturally, any desired opening of any desired shape may be provided which allows the gaseous solvent to leave the container 10 during lyophilization. The opening 45 is provided at a defined spacing A (shown by the double arrow in FIG. 1) from the bottom of the separating stopper 40, so that the stopper 40 closes off the upper end 70 but not the opening 45 (first position).

Subsequently, freeze drying is carried out in the usual way in the lyophilizer, with the solvent evaporating from the lyophilization solution through the opening 45. Then after the lyophilization the sealing is carried out in the lyophilizer by pushing in and inserting the separating stopper 40 into the upper end 70. This is shown in FIG. 4. In other words while still in the lyophilizer the separating stopper 40 is pressed down into a position in which it is disposed above the lyophilizate cake 30 obtained and above the bypass 35. To some extent this may be done by pushing together the plates on which the containers are standing. The container 10 may be sealed under vacuum, so that it is possible subsequently to push the separating stopper 40 further into the cylindrical body, optionally in a filling machine, without causing excess pressure in the already sealed chamber. By pushing the separating stopper 40 into the cylindrical body 10 the opening 45 in the separating stopper is closed off by the inner walls, so that the sealing function of the separating stopper 40 is not affected by the opening 45.

The containers 10 are then taken out of the lyophilizer. Then reconstituting medium is introduced through the now re-opened end 70. Finally, the container 10 is closed off with a closure 60 such as an end stopper (FIG. 5). If in order to mix together the two components pressure is exerted on the closure or end stopper 60, this moves in the direction of the separating stopper 40. The separating stopper 40 which separates the chamber 50 containing the liquid component of the two-chamber system from the chamber 30 containing the solid component is preferably constructed like a conventional separating stopper at its side face which forms a seal with the wall of the cylindrical body 15. If the adhesive friction of the separating stopper 40 on the wall of the cylindrical body 15 is not sufficient for the intended purpose, i.e., to prevent undesirable slipping or movement of the separating stopper 40, the latter may preferably be additionally held by means of small bumps (not shown) on the inner surface of the cylindrical body 15.

As pressure continues to be applied the separating stopper 40 finally moves to the bypass 35 and thereby opens up access for the liquid component into the chamber 30. As a result a lyophilizate is reconstituted.

Figure 6:
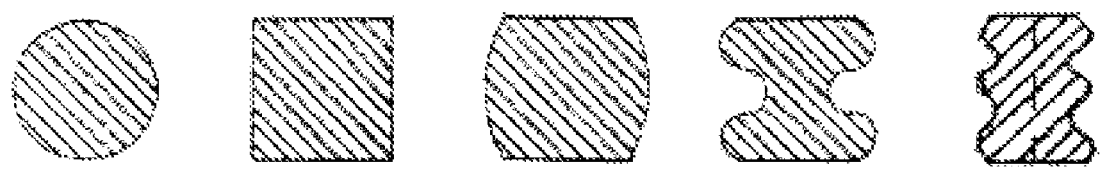
FIG. 6 shows different variants of stoppers according to the invention.

The separating stopper 40 may have any suitable shape and size provided that it is displaceable. It may, for example, as shown in FIGS. 1 to 5, have various convexities in the form of large bumps. However, it may also be in the form of a cylinder or a cylinder with a spherical outer shape or dumbbell shape with two sealing surfaces, as shown by way of example in FIG. 6.

FIG. 7a shows a variant of the stopper 40 with an opening 45 in the side face provided at a defined distance from the top surface of the stopper. This opening 45 leads to an interior channel 85 that terminates on the opening 80 in the bottom surface of the separating stopper 40. FIG. 7b is a side wise cross sectional view of the stopper shown in FIG. 7a.

FIG. 7c shows another variant of the stopper 40 with an exterior channel 90 on the side face of the stopper provided at a given distance from the top surface of the stopper 40 and extending upto its bottom surface. FIG. 7d is a cross sectional profile of the stopper shown in FIG. 7c.

The foregoing description of the Figures serves to illustrate the apparatus according to the invention and the process according to the invention. This is intended purely as a possible procedure described by way of example without restricting the invention to its contents.

What is claimed is:

1. A double chamber container for separately holding and combining a solid lyophilizate and a liquid reconstituting medium therefor, comprising
    a cylindrical body extending in a longitudinal direction, with a closure at each of the two ends of the body, an upper displaceable closure at the reconstituting medium end, and a lower closure at the lyophilizate end,
    a separating stopper which can be pushed along by the application of pressure, in the cylindrical body and acting as a seal between the upper chamber and the lower chamber, the separating stopper having
        a top surface, a bottom surface, and a side face extending between the top and bottom surfaces, and
        at least one opening in the side face provided at a first defined distance from the top surface and a second defined distance from the bottom surface, the at least one opening leading to a channel extending inside of the separating stopper in a longitudinal direction from the at least one opening to the bottom surface, characterized in that the first and second defined distances are selected so that the separating stopper can assume two positions, wherein in a first position within an upper end of the cylindrical body, the separating stopper closes off the upper end of the cylindrical body without closing off the least one opening; and
    a bypass arranged underneath the separating stopper, with a length L that is preferably greater than the height H of the separating stopper.

2. Double chamber container according to claim 1, the stopper in a second position tightly seals off the upper end of the cylindrical body.

3. Double chamber container according to claim 1, characterized in that at least two openings are arranged in a pair or symmetrically in the separating stopper.

4. Double chamber container according to claim 1, characterized in that the at least two openings are arranged below one another or side by side.

5. Double chamber container according to claim 1, characterized in that the lyophilizate is a pharmaceutical composition.

6. Double chamber container according to claim 1, characterized in that the reconstituting medium is a dissolving or a dispersing medium for the lyophilizate.

7. Process for mixing a solid lyophilizate and a liquid reconstituting medium therefor in a double chamber container, comprising:
    a cylindrical body with a closure at each of the two ends of the body, a movable upper closure, particularly a stopper, at the reconstitution medium end and a lower closure at the lyophilizate end,
    a separating stopper which can be moved by the application of pressure in the cylindrical body as a seal between the upper chamber and the lower chamber, the separating stopper having:
        a top surface, a bottom surface, and a side face, and one or more openings in the side face provided at a first defined distance from the top surface and a second defined distance from the bottom surface, the one or more openings leading to one or more channels extending inside of the separating stopper in a longitudinal direction from the one or more openings through the bottom surface, characterized in that the first and second defined distances are selected so that the separating stopper can assume two positions, wherein in a first position within an upper end of the cylindrical body, the separating stopper closes off the upper end of the cylindrical body without closing off the least one opening;
        a bypass arranged underneath the separating stopper, with a length L that is preferably greater than the height H of the separating stopper.

8. Process according to claim 7, characterized in that during a mixing process the cylindrical body is held vertically with the closure at the bottom.

9. Process according to claim 7, characterized in that the closure, particularly a stopper at the upper end is pressed forward as far as the separating stopper.

* * * * *